United States Patent [19]

Pawlowski et al.

[11] Patent Number: 5,064,959

[45] Date of Patent: Nov. 12, 1991

[54] AROMATIC COMPOUNDS SUBSTITUTED BY 4,6-BIS(TRICHLOROMETHYL)-S-TRIAZIN-2-YL GROUPS

[75] Inventors: Georg Pawlowski, Wiesbaden; Fritz Erdmann, Eltville; Heidrun Lutz, Mainz, all of Fed. Rep. of Germany

[73] Assignee: Hoechst Aktiengesellschaft, Frankfurt am Main, Fed. Rep. of Germany

[21] Appl. No.: 317,562

[22] Filed: Mar. 1, 1989

[30] Foreign Application Priority Data

Mar. 7, 1988 [DE] Fed. Rep. of Germany ....... 3807378

[51] Int. Cl.$^5$ .......................................... C07D 251/20
[52] U.S. Cl. ..................................................... 544/216
[58] Field of Search ........................................ 544/216

[56] References Cited

U.S. PATENT DOCUMENTS

| 4,189,323 | 2/1980 | Buhr | 430/281 |
| 4,619,998 | 10/1986 | Buhr | 544/193.1 |
| 4,696,888 | 9/1987 | Buhr | 430/270 |

FOREIGN PATENT DOCUMENTS

WO81/02261 8/1981 World Int. Prop. O.

OTHER PUBLICATIONS

Wakabayashi et al., "Studies on s-Triazines. I. Cotrimerization of Trichloroacetonitrile with Other Nitriles", Bulletin of the Chemical Society of Japan, vol. 42, 1969, pp. 2924–2930.

Primary Examiner—John M. Ford
Attorney, Agent, or Firm—Foley & Lardner

[57] ABSTRACT

Compounds of general formula

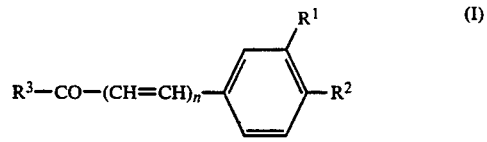

are disclosed in which $R^1$ and $R^2$ are different from one another and denote either a hydrogen atom or a radical of the formula

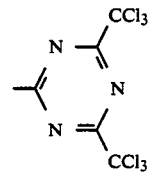

$R^3$ denotes a substituted or unsubstituted alkoxy, alkenyloxy, alkynyloxy or aryloxy radical, a hydroxyl group or a halogen atom and n the number 0 or 1.

The compounds are useful intermediates for the preparation of photoinitiators and are themselves active as photoinitiators.

17 Claims, No Drawings

AROMATIC COMPOUNDS SUBSTITUTED BY 4,6-BIS(TRICHLOROMETHYL)-S-TRIAZIN-2-YL GROUPS

BACKGROUND OF THE INVENTION

The present invention relates to aromatic 4,6-bis(trichloromethyl)-s-triazin-2-yl compounds, a process for their preparation and their use as photoinitiators in light-sensitive mixtures. The compounds according to the invention are also useful intermediates for the preparation of highly-active photoinitiators or photolytically-active acid donors for light-sensitive mixtures.

4,6-Bis(trichloromethyl)-s-triazin-2-ylphenyl compounds are known in many forms; a detailed description of various compounds of this type is provided by M. Wakabayashi et al., Bull. Chem. Soc. Jpn., 42, 2924 (1969). The phenyl ring in these compounds can be substituted by relatively inert chemical groupings, such as, for example, nitro, alkyl or alkoxy groups or halogen atoms.

WO 81/02262 discloses light-sensitive mixtures containing 4,6-bis(trichloromethyl)-s-triazin-2-ylphenyl derivatives as photoinitiators in which the aromatic ring is substituted by 1 to 3 alkyl or alkoxy groups. The light-sensitive mixtures described are used for the preparation of pressure-sensitive adhesive tape. The photoactivity of these compounds is in the near UV region.

The above-mentioned 4,6-bis(trichloromethyl)-s-triazin-2-ylphenyl derivatives are not important in practice as intermediates, since they cannot be further reacted or can only be further reacted with at least partial destruction of the trichloromethyl groups.

On the other hand, it is known that certain 4,6-bis(trichloromethyl)-s-triazin-2-yl derivatives have very good properties as photoinitiators and photolytic acid donors. Examples of this type of compound are known from DE-C 2,718,259, in which substituted or unsubstituted 4,6-bis(trichloromethyl)-s-triazin-2-ylnaphthyl derivatives are described, or from EP-A 0,137,452 from which substituted or unsubstituted 4,6-bis(trichloromethyl)-s-triazin-2-ylstyrylphenyl derivatives which can be used as photoinitiators originate. Although the compounds mentioned in this publication are highly active in the near UV region and to some extent also in the visible region, they have the disadvantage that their preparation is frequently very complicated, expensive and time-consuming.

There is therefore a demand for novel 4,6-bis(trichloromethyl)-s-triazin-2-yl derivatives that can be converted with comparative synthetic ease while maintaining the trichloromethyl groups intact into chromophore-substituted compounds having high photoactivity as initiators in photopolymerizable mixtures or as acid donors in mixtures which can be cleaved by acid in the near UV region or in the visible region.

SUMMARY OF THE INVENTION

It is therefore an object of the present invention to provide novel 4,6-bis(trichloromethyl)-s-triazin-2-ylphenyl derivatives that can be prepared in a simple and inexpensive manner and that can be converted easily into chromophore-substituted photoinitiators having high activities in the industrially important regions of the electromagnetic spectrum.

The invention relates to compounds of general formula I

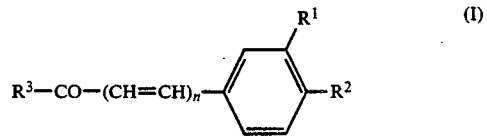

in which
R$^1$ and R$^2$ are different from one another and denote either a hydrogen atom or a radical of the formula

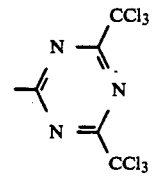

R$^3$ denotes a substituted or unsubstituted alkoxy, alkenyloxy, alkynyloxy or aryloxy radical, a hydroxyl group or a halogen atom and
n denotes the number 0 or 1.

Furthermore, according to the invention, a process for the preparation of compounds of the above-mentioned formula I is proposed comprising the steps of reacting a compound of the formula II

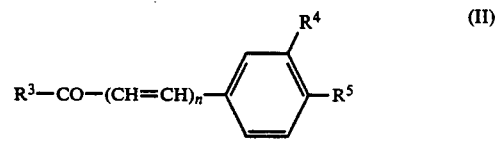

in which R$^3$ and n have the above-mentioned meaning and R$^4$ and R$^5$ are different from one another and denote either a hydrogen atom or a CN group, with trichloroacetonitrile under the influence of HCl gas in the presence of a Lewis acid.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

The compounds according to the present invention are light-sensitive and are suitable as photoinitiators or as photolytic acid donors in light-sensitive mixtures. For this purpose, preference is given to compounds of the formula I in which R$^3$ denotes a substituted or unsubstituted alkoxy, alkenyloxy, alkynyloxy or aryloxy radical. Of these, the compounds having n=1 are particularly suitable.

The compounds of the formula I, in particular those in which R$^3$ denotes halogen, are useful intermediates for the preparation of light-sensitive compounds having a high activity in the visible and near ultraviolet region of the electromagnetic spectrum. They can be easily reacted via the acid chloride group with reactive aromatic, heterocyclic or olefinic compounds with the formation of a conjugated system of any desired length, while the photoactive trichloromethyl groups on the triazine ring remain intact.

An example of this type of synthesis is the preparation of oxadiazole derivatives by reaction of I with compounds

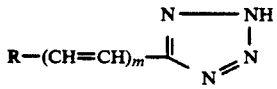

to give oxadiazole derivatives

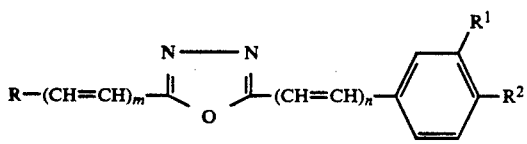

in which R is a substituted or unsubstituted aryl or heteroaryl radical and m is zero or 1. These compounds have been described in more detail in application Ser. No. 07/317,560 (corresponding to German application P 3,807,380.3), filed concurrently with the present application. The contents of this copending application are hereby incorporated by reference.

Furthermore, compounds of the formula I can be reacted with compounds of the formula

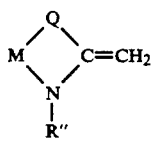

or the minimum salt thereof

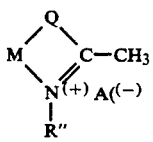

to give compounds of the formula

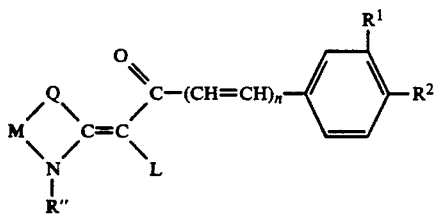

in which

R″ denotes an alkyl, aralkyl, aryloxyalkyl or alkoxyalkyl radical,

L denotes a hydrogen atom or a substituent of the formula

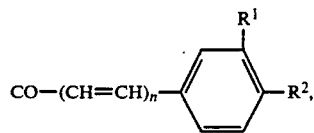

M denotes a substituted or unsubstituted alkylene radical or alkenylene radical or a 1,2-arylene radical and Q denotes a sulfur, selenium or oxygen atom, a dialkylmethylene group, an alken-1,2-ylene radical, a 1,2-phenylene radical or a group N-R″, in which M+Q together form 3 or 4 ring members. These compounds have been described in more detail in application Ser. No. 07/317,595 now U.S. Pat. No. 4,958,957, (corresponding to German application P 3,807,381.1), filed concurrently with the present application. The contents of this copending application are hereby incorporated by reference.

Of the compounds of the formula I in which $R^3$ together with the carbonyl group forms an ester group, in general those compounds are preferred in which $R^3$ denotes an alkoxy radical having 1 to 16 carbon atoms that is unsubstituted or substituted by halogen atoms, an alkenyloxy radical having 2 to 6 carbon atoms, an alkynyloxy radical having 2 to 6 carbon atoms, an alkoxyalkoxy radical having 3 to 10 carbon atoms, an aryloxy radical having 6 to 14 carbon atoms which is unsubstituted or substituted by halogen, alkyl, alkoxy or nitro groups or denotes an aryloxyalkoxy radical having 8 to 12 carbon atoms.

Of these compounds, those are particularly preferred in which $R^3$ denotes an alkoxy group having 1 to 6 carbon atoms, an alkenyloxy group having 2 to 4 carbon atoms or an alkynyloxy group having 2 to 4 carbon atoms.

If $R^3$ is a halogen atom, it is in particular a chlorine atom.

Preferred compounds include 3-(4,6-bis(trichloromethyl)-s-triazin-2-yl)benzoic acid and its methyl ester, ethyl ester and acid chloride; 4-(4,6-bis(trichloromethyl)-s-triazin-2-yl)benzoic acid and its methyl ester, ethyl ester and acid chloride; 3-(4,6-bis(trichloromethyl)-s-triazin-2-yl)cinnamic acid and its methyl ester, ethyl ester and acid chloride; 4-(4,6-bis(trichloromethyl)-s-triazin-2-yl)cinnamic acid and its methyl ester, ethyl ester and acid chloride. Of these, the compounds in which n is 0 are very particularly preferred.

The compounds according to the invention of general formula I are in general crystalline, colorless to yellowish-colored substances which, in the absence of light and/or moisture, can be stored for a virtually unlimited period of time.

For the preparation of the compounds according to the invention of general formula I, various procedures are possible which, depending on the type of the compound used, give different results with respect to yield or space-time yield.

In scheme I described below, the various preparation methods are listed schematically, R' representing one of the organic radicals listed under $R^3$.

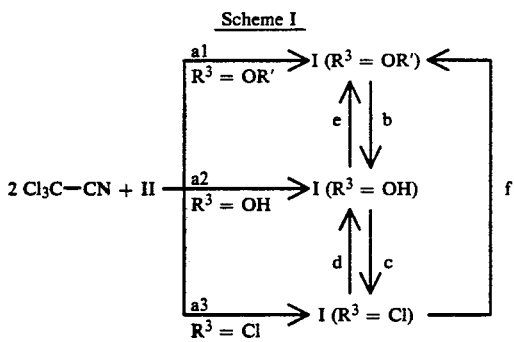

Scheme I

Preparation Process for Compounds in Which R³ is OR'

Method a1

By cotrimerization of trichloroacetonitrile with the corresponding 3- or 4-cyanobenzoic or -cinnamic esters with hydrogen chloride gas in the presence of a Lewis acid [analogously to K. Wakabayashi et al., *Bull. Chem. Soc. Jpn.*, 42. 2924 (1969)]:

The 3- or 4-cyanobenzoic or -cinnamic ester, preferably the corresponding methyl or ethyl ester, is dissolved or suspended in an about 2- to 10-fold, preferably about 6-fold, excess of trichloroacetonitrile at temperatures of about 10 to 50° C., preferably about 20 to 30° C. If the ester is not soluble in trichloroacetonitrile, the reaction can also be carried out with the addition of a suitable, acid-resistant solvent, for example dichloromethane. The solution or suspension is stirred at a temperature between about −20 and +50° C., preferably at about 25° C., in the absence of moisture. With sufficient cooling, a Lewis acid, for example aluminum chloride, boron trichloride etherate, tin chloride or zinc chloride, preferably aluminum bromide, is added in a molar ratio of about 1:5 to 1:50, preferably around 1:10, relative to the ester, and anhydrous hydrogen chloride is introduced. The energy released in the form of heat is removed by cooling. The introduction of hydrogen chloride is stopped after about 2 to 20, preferably about 3 to 6 hours, and the reaction product which solidifies is allowed to react further at room temperature, if necessary with slight cooling. After about 5 to 100 hours, the evolution of hydrogen chloride has subsided, and the reaction is complete. The catalyst and the excess acid are removed by taking up the reaction product in an inert solvent, preferably dichloromethane, and extracting the mixture with the same volume of water. The organic phase is dried and concentrated and the already very pure product, which in general is formed as crystals, is processed, if necessary, by suitable purification measures.

Method e

By extractive esterification of the 3- or 4-(4,6-bis(trichloromethyl-s-triazin-2-yl)-benzoic or -cinnamic acid prepared according to method a2:

The 3- or 4-(4,6-bis(trichloromethyl-s-triazin-2-yl)-benzoic or -cinnamic acid is dissolved or suspended in an about 2- to 50-fold amount of a solvent which forms an azeotrope with water, such as dichloromethane, trichloromethane, toluene or xylene. An acid catalyst, for example sulfuric acid, naphthalenesulfonic acid, an acidic ion-exchange resin or preferably toluenesulfonic acid, is added in a molar ratio of about 1:100 to 1:10, preferably of about 1:30 to 1:15, relative to the acid to be esterified, and the anhydrous alcohol, preferably an alcohol having more than 1 carbon atom, is added in about a 1.2- to 12-fold excess, preferably about 2-fold excess, to the mixture. The mixture is heated to about 35 to 170° C., preferably about 75 to 140° C., and the water which is formed is separated through a suitable separator. The formation of water is usually finished after about 2 to 24 hours. The mixture is cooled to about 10 to 25° C. and is washed with a dilute weakly alkaline salt solution, preferably an aqueous sodium bicarbonate solution, and the organic phase is treated as described above.

To prepare the methyl ester, the benzoic or cinnamic acid derivative is suspended in an about 2- to 20-fold, in general about 3- to 8-fold, amount of anhydrous methanol, and sulfuric acid or preferably toluenesulfonic acid is added in the above-mentioned molar ratio. If desired, a water-immiscible solvent that does not form an azeotrope, for example a dialkyl ether, or one of the above-mentioned solvents that forms an azeotrope can be added in the 2- to 10-fold amount. The mixture is heated to about 30 to 100° C. for about 2 to 20 hours, in most cases for about 4 to 8 hours. The excess alcohol is separated, and the residue is taken up in a water-immiscible organic solvent, preferably a halohydrocarbon or ether, and treated as described above.

Method f

By esterification of the 3- or 4-(4,6-bis(trichloromethyl)-s-triazin-2-yl)-benzoyl or -cinnamoyl chloride prepared according to method a3:

The corresponding acid chloride is dissolved in an about 5- to 20-fold amount of inert, anhydrous solvent, for example dichloromethane, toluene or tetrahydrofuran. The desired alcohol or a phenol is added to this solution in about a 1.1- to 5-fold, preferably about 1.1 to 1.5-fold, excess. The mixture is stirred at a temperature between about −15° C and +50° C. If the alcohol is an unsaturated alcohol, a temperature range between about −15° C. and 15° C. is preferred; if the alcohol is saturated, a temperature range from about +5° C. to 35° C. is preferred. About a 1.1- to 5-fold, preferably about a 1.1- to 1.5-fold, excess, relative to the acid chloride, of an acid-binding agent, such as pyridine or triethylamine, is added dropwise, while maintaining the temperature constant by cooling. Stirring of the mixture at the temperature given is continued for about 1 to 10 hours, in most cases about 3 hours, and the mixture is then allowed to warm or cool to room temperature. The resulting salts are separated, and the mixture diluted, if necessary, with a water-insoluble solvent, for example diethyl ether, dichloromethane or toluene, is worked up as described in method e.

Preparation process for compounds in which R³ is OH

Method a2

The procedure as described under method a1 is repeated, using 3- or 4-cyanobenzoic or -cinnamic acid. Since the acids are often not soluble enough in trichloroacetonitrile, the reaction must be carried out in a suspension or with the addition of an organic, inert solvent. In both cases, the reaction then proceeds very slowly. Therefore, the process has only limited significance for the preparation of the 3- or 4-(4,6-bis(trichloromethyl)-s-triazin-2-yl)benzoic or -cinnamic acid derivatives.

Method b:

By transesterification of methyl 3- or 4-(4,6-bis(trichloromethyl)-s-triazin-2-yl)benzoate or -cinnamate with trichloroacetic acid in the presence of a strong mineral acid:

To the methyl ester, preferably the corresponding methyl benzoate, is added about a 0.5- to 10-fold, preferably about 2-fold, amount of trichloroacetic acid. A catalytic amount, preferably in a ratio around 1:50, relative to the ester, of a strong inorganic acid, preferably sulfuric acid, is added to the mixture. The mixture is heated to about 130 to 190° C., preferably about 150 to 180° C., and the resulting methyl trichloroacetate is separated by distillation. After 60 to 90% of the theoretical amount has come over, the mixture is allowed to cool to about 50 to 120° C., preferably about 50 to 90° C., and poured into ice water, as a result of which the desired acids precipitate. The mixture obtained is stirred for about 10 to 30 minutes, filtered with suction and the solid is washed with a sufficient amount of water. The acid obtained can be purified by recrystallization.

By conversion of methyl or ethyl 3- or 4-(4,6-bis(trichloromethyl)-s-triazin-2-yl) benzoate or cinnamate to the corresponding trimethylsilyl esters followed by hydrolysis:

The ester, preferably a methyl ester, is dissolved in about a 2- to 20-fold amount of an inert, dry solvent, preferably chloroform or 1,2-dichloroethane. Under a nitrogen atmosphere, about a 1- to 3-fold, preferably about 1.5-fold, excess of hexamethyldisilane and then the equivalent amount of iodine are added. The mixture warms up and is heated to a temperature between about 60 and 150° C., preferably about 85° C., for about 2 to 48 hours, in particular about 4 to 10 hours. The resulting brownish mixture is allowed to cool to about 0 to 50° C., preferably about 10 to 20° C., and about a 0.5- to 5-fold amount, preferably about the same amount by volume, of ice water is added. After stirring for about 10 to 60 minutes, the solvent is evaporated and the remaining precipitate is triturated in an alcohol, preferably methanol. The resulting product is isolated by filtration and, if desired, purified by recrystallization.

Method d

This method hydrolyzes the corresponding 3- or 4-(4,6-bis(trichloromethyl)-s-triazin-2-yl)benzoyl or -cinnamoyl chloride. It proceeds very well, but is without practical significance, since the corresponding acid chlorides are preferably prepared from the acids.

Preparation process for compounds in which $R^3$ is Cl

Method a3

The procedure as described under method a1 is repeated, using 3- or 4-cyanobenzoyl- or -cinnamoyl chloride. Due to the high reactivity of the acid chloride groups, purification of the products in this procedure is only possible by high vacuum distillation. Therefore, the process has less practical significance.

Method c

By reaction of 3- or 4-(4,6 -bis(trichloromethyl)-s-triazin-2-yl)benzoic or -cinnamic acid with thionyl chloride:

About a 2- to 6-fold, preferably about a 2.5- to 4-fold, amount by weight of thionyl chloride is added to the corresponding acid, and the mixture is heated to about 50 to 100° C., preferably about 80° C., until no more evolution of $SO_2$ is observed. After about 2 to 20 hours, for example about 6 hours, the excess thionyl chloride is distilled. The acid chloride that is contained in the residue can be purified by recrystallization.

This discussion makes clear that for producing the ester derivatives of general formula I the preferred processes are routes a1, e and f; for producing the acid derivatives the preferred process is route b; and for producing the acid chlorides the preferred process is route c. The individual classes of compounds can be interconverted by simple preparative methods.

Despite analogous processes known from the literature for the preparation of bis(trichloromethyl)triazine derivatives, the successful outcome of the trimerization described above to give the compounds according to the invention of general formula I was by no means self evident, since it appeared likely that, for example, the esters might be cleaved under the trimerization conditions. Because of the low solubility of the acids, no cotrimerization tendency was expected. It appeared likely that if chlorides were used, acylation side reactions would take place.

The compounds according to the invention of general formula I are novel and are suitable in an advantageous manner as photoinitiators in photopolymerizable mixtures, it being possible to sensitize them spectrally by means of suitable dyes. Thus, they are suitable, for example, as coinitiators in photopolymerizable mixtures in combination with particular heterocyclic initiators and, if desired, photoreducible dyes. Thus, they can be, for example, advantageously used in photopolymerizable mixtures of polymerizable (meth)acrylic esters, photoreducible dyes and/or acridine, phenazine or quinoxaline compounds, such as have been described in German Patent Applications P 3,710,281.8, P 3,710,282.6, P 3,743,454.3, P 3,743,455.1 and P 3,743,457.8, instead of the trichloromethyl compounds mentioned in these publications.

The most important application of the compounds according to the invention, in particular those in which $R^3$ is halogen, resides in the fact that they can be used as useful intermediates for the preparation of highly-active novel photoinitiators or photolytic acid donors, for example of compounds based on oxadiazole or based on carbonylmethylene heterocycles which can be prepared by the processes of Application Serial Nos. 07/317,560 and 07/317,595, now U.S. Pat. No. 4,958,957(corresponding to German Patent Applications P 3,807,380.3 and P 3,807,381.1, respectively).

Because of the favorable initiator properties of trichloromethyl-substituted compounds according to the invention of general formula I and also in particular because of the easy access thus made possible to further extremely useful photoinitiators and photolytic acid donors, the present invention represents a considerable enrichment of the art and significant progress.

The examples described below are intended to illustrate the present invention in more detail. Percentages and amount ratios are by weight, unless noted otherwise. The amounts are usually given in parts by weight (pw).

EXAMPLE 1

Preparation of methyl
4-(4,6-bis(trichloromethyl)-s-triazin-2-yl) benzoate
(method a1)

Methyl 4-cyanobenzoate (16 pw) are stirred with trichloroacetonitrile (86.6 pw) and aluminum bromide (3.2 pw) in the absence of moisture. The temperature of the clear solution is kept constant at 24 to 28° C., and hydrogen chloride gas is then passed into the solution with stirring until no more HCl absorption takes place (about 2 to 5 hours). The reaction product solidifies more and more during this time. Stirring is discontinued, and the syrup-like mixture is allowed to further react at room temperature for 24 hours. The yellow, solid reaction product is taken up in 500 pw of dichloromethane and washed twice with 250 pw each of distilled water. The organic phase is dried over sodium sulfate. After evaporation of the solvent, the white residue is recrystallized from 250 pw of ethanol. Yield: 41 pw 91% of theory of white crystals of methyl 4-(4,6-bis(trichloromethyl)-s-triazin-2-yl)benzoate. M.p.: 157 to 158° C.

$C_{13}H_7N_3Cl_6O_2$ (449.9)

Calc. C 34.70%, H 1.51%, N 9.34%, Cl 47.28%.
Found C 34.6%, H 1.4%, N 9.1%, Cl 47.7%.

The methyl 4-cyanobenzoate used as starting compound can be prepared as follows:

Pyridine (16 pw) is added to hydroxylamine hydrochloride (14 pw), and the mixture is stirred. 4-Methoxycarbonylbenzaldehyde (32.8 pw) is added with stirring, causing the mixture to warm. After 10 minutes, 200 pw of m-xylene are added, and the mixture is heated to reflux in a water separator. After about 10 hours, the theoretical amount of water has separated. The mixture is allowed to cool to room temperature, is diluted with 200 pw of diethyl ether and washed twice with 150 pw each of distilled water. The organic phase is dried over magnesium sulfate, and the solvents are removed on a rotary evaporator, the last traces of xylene being evaporated under reduced pressure. The crude product obtained, mainly composed of methyl 4-cyanobenzoate, is recrystallized from 150 pw of ethanol.

EXAMPLE 2

Preparation of methyl
3-(4,6-bis(trichloromethyl)-s-triazin-2-yl)benzoate
(method a1)

Methyl 3-cyanobenzoate (70 pw) are mixed with trichloroacetonitrile (376 pw) and aluminum bromide (13.9 pw) as described in Example 1, step 2, hydrogen chloride gas is added, the mixture is allowed to react and the reaction product is separated. Recrystallization from ethanol gives 160 pw=82% of white crystals of methyl 3-(4,6-bis(trichloromethyl)-s-triazin-2-yl)benzoate. M.p.: 115 to 117° C.

$C_{13}H_7N_3Cl_6O_2$ (449.9)

Calc. C 34.70%, H 1.51%, N 9.34%, Cl 47.28%.
Found C 34.4%, H 1.5%, N 9.4%, Cl 47.1%.

The methyl 3-cyanobenzoate used as starting compound can be prepared as follows: thionyl chloride (240 pw) and toluene (240 pw) are mixed, and 140 pw of 3-cyanobenzoic acid are added. The suspension is stirred in the absence of moisture and heated to reflux. After about 5 hours the evolution of $SO_2$ is complete, and the solution is clear. Excess thionyl chloride and toluene are distilled, and the residue is poured carefully into 600 pw of methanol. The mixture is left to stand for 24 hours and then cooled to 0° C. to complete the precipitation. The precipitate of methyl 3-cynobenzoate is filtered off with suction and dried over phosphorus pentoxide.

EXAMPLE 3

Preparation of methyl
4-(4,6-bis(trichloromethyl)-s-triazin-2-yl)cinnamate
(method a1)

Methyl 4-cyanocinnamate (46 pw) is suspended in the absence of moisture and at 24 to 28° C. in a mixture of trichloroacetonitrile (208.2 pw) and aluminum bromide (7.68 pw). The mixture is stirred, and hydrogen chloride is introduced at constant temperature. Temporarily, an almost clear solution is formed, but soon thereafter the mixture becomes syrup-like. Introduction of hydrogen chloride gas is stopped after 4 hours, stirring is discontinued and the mixture is maintained at 28° C. for 12 hours. The resulting solid material is dissolved in 500 pw of dichloromethane and washed twice with 250 pw of water. The organic phase is dried over calcium chloride, and the solvent is evaporated. The residue is recrystallized from a 1:1 mixture of methanol and 2-methoxyethanol.

Yield: 81.1 pw=72%, white needles having a melting point of 162 to 163° C.

$C_{15}H_9N_3O_2Cl_6$ (475.9)

Calc. C 37.85%, H 1.91%, N 8.83%, Cl 44.69%.
Found C 37.3%, H 1.7%, N 9.0%, Cl 45.2%.

The 4-cyanocinnamic acid used as starting substance can be prepared as follows:

4-Cyanocinnamic acid (50 pw), absolute methanol (27.7 pw), 1,2-dichloroethane (200 pw) and toluenesulfonic acid (1.6 pw) are heated to reflux for about 15 hours. Monitoring at this point by thin-layer chromatography shows that the reaction has gone to completion. The clear solution is cooled with ice, after which some of the product crystallizes and is isolated by filtration. The mother liquor is washed with 5% strength sodium bicarbonate solution and washed twice with water. After drying of the organic phase over magnesium sulfate, the solvent is evaporated and the resulting product is dried over phosphorus pentoxide. The two batches of methyl 4-cyanocinnamate are combined, since both have the same purity.

EXAMPLE 4

Preparation of methyl
3-(4,6-bis(trichloromethyl)-s-triazin-2-yl)cinnamate
(method a1)

Methyl 3-cyanocinnamate (42 pw) is added to a mixture of trichloroacetonitrile (194.4 pw) and aluminum bromide (7.2 pw) in the absence of moisture and at about 25° C. Hydrogen chloride is then introduced over a period of 3 hours with stirring, while keeping the temperature constant. Stirring is discontinued, and the mixture is allowed to react further overnight. In this step, too, a constant temperature of 25° C. is maintained. The solidified mixture is dissolved in 800 pw of dichloromethane, washed with water, and the organic phase is dried over sodium sulfate. Evaporation of the solvent gives a white residue, which is recrystallized from methanol or benzene.

Yield: 92 pw=86.3% of theory of white needles having a melting point of 118.5 to 119.5° C.

$C_{15}H_9N_3O_2Cl_6$ (475.9)

Calc.: C 37.85%, H 1.91%, N 8.83%, Cl 44.69%
Found: C 37.9%, H 1.9%, N 9.0%, Cl 44.9%.

The methyl 3-cyanocinnamate used can be prepared as follows:

3-Cyanocinnamic acid (105 pw), absolute methanol (58 pw), 1,2-dichloroethane (350 pw) and toluenesulfonic acid (2.2 pw) are refluxed for 35 hours. Since even after this time no complete conversion is observed, the mixture is allowed to cool, is washed twice with 5% strength sodium hydroxide solution and then with water. The organic phase is dried over sodium sulfate, and the residue of methyl 3-cyanocinnamate after being freed from the solvent is dried over phosphorus pentoxide.

EXAMPLES 5 to 15

According to Examples 1 to 4, the following compounds are prepared (methods a1, a2 and a3; methods a2 and a3 correspond to method a1, except that in the final treatment according to method a2 the organic phase is washed several times with a fairly large amount of water and, according to method a3, separation of the reaction mixture is carried out by high vacuum distillation).

EXAMPLE 5

Ethyl 4-(4,6-bis(trichloromethyl)-s-triazin-2-yl)-benzoate, m.p. 101 to 102° C. (method a1).

EXAMPLE 6

Ethyl 3-(4,6-bis(trichloromethyl)-s-triazin-2-yl)benzoate, m.p. 114.5 to 115.5° C. (method a1).

EXAMPLE 7

Ethyl 4-(4,6-bis(trichloromethyl)-s-triazin-2-yl)cinnamate, m.p. 134.5 to 135.5° C. (method a1).

EXAMPLE 8

Ethyl 3-(4,6-bis(trichloromethyl)-s-triazin-2-yl)cinnamate, m.p. 99 to 100° C. (method a1).

EXAMPLE 9

2-Chloroethyl 4-(4,6-bis(trichloromethyl)-s-triazin-2-yl)benzoate, m.p. 108 to 109° C. (method a1).

EXAMPLE 10

Phenyl 4-(4,6-bis(trichloromethyl)-s-triazin-2-yl)benzoate, m.p. 148 to 150° C. (method a1).

EXAMPLE 11

2-Phenylethyl 4-(4,6-bis(trichloromethyl)-s-triazin-2-yl)benzoate, m.p. 113 to 115° C. (method a1).

EXAMPLE 12

4-(4,6-Bis(trichloromethyl)-s-triazin-2-yl)benzoic acid, m.p. 275° C. (method a2).

EXAMPLE 13

3-(4,6-Bis(trichloromethyl)-s-triazin-2-yl)cinnamic acid, m.p. 210 to 211° C. (method a2).

EXAMPLE 14

4-(4,6-Bis(trichloromethyl)-s-triazin-2-yl)benzoyl chloride, m.p. 100 to 101° C. (method a3).

EXAMPLE 15

4-(4,6-Bis(trichloromethyl)-s-triazin-2-yl)cinnamoyl chloride, m.p. 156 to 157° C. (method a3).

EXAMPLE 16

Preparation of 4-(4,6-bis(trichloromethyl)-s-triazin-2-yl)benzoic acid (method b)

Methyl 4-(4,6-bis(trichloromethyl)-s-triazin-2-yl)benzoate (125 pw), trichloroacetic acid (250 pw) and concentrated sulfuric acid (2 pw) are heated to 175° C. with stirring. At this temperature, the methyl trichloroacetate formed is removed by distillation. After about 40 pw of methyl trichloroacetate have been distilled, a slight vacuum of 270 mbar is established to complete the distillation. The residue is allowed to cool to 80° C. and then added to 1500 pw of ice water. The mixture is triturated for 30 minutes, and the product is then removed by filtration with suction.

Yield: 87 pw=72% of theory, white crystals (from toluene) of m.p. 275° C.

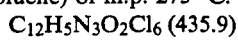$C_{12}H_5N_3O_2Cl_6$ (435.9)

Calc.: C 33.06%, H 1.16%, N 9.64%, Cl 48.80%.
Found: C 33.3%, H 1.0%, N 9.6%, Cl 48.3%.

EXAMPLE 17

Preparation of 3-(4,6-bis(trichloromethyl)-s-triazin-2-yl)benzoic acid (method b)

Analogously to Example 16, 106 pw=91% of theory of 3-(4,6-bis(trichloromethyl)-s-triazin-2-yl)benzoic acid of melting point 211.5° C. (benzene/toluene 10:1) are obtained from 120 pw of methyl 3-(4,6-bis(trichloromethyl)-s-triazin-2-yl)benzoate.

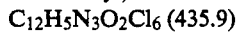$C_{12}H_5N_3O_2Cl_6$ (435.9)

Calc.: C 33.06%, H 1.16%, N 9.64%, Cl 48.80%.
Found: C 33.1%, H 1.0%, N 9.6%, Cl 49.2%.

EXAMPLE 18

Preparation of 4-(4,6-bis(trichloromethyl)-s-triazin-2-yl)cinnamic acid (method b)

In a flask flushed with dry nitrogen are placed 450 pw of dry 1,2-dichloroethane, 49.2 pw of hexamethyldisilane and 85.3 pw of iodine. Methyl 4-(4,6-bis(trichloromethyl)-s-triazin-2-yl)cinnamate (80 pw) is added in portions, during which the reaction sometimes proceeds exothermically and is kept under control by cooling. After the addition is complete, the mixture is heated to reflux using a cooling system operating at −20° C., which is continued until thin-layer chromatography indicates a virtually complete conversion (4 to 12 hours). After cooling, 400 pw of water are added to the reaction mixture, which is concentrated on a rotary evaporator until the dichloroethane has been evaporated. Methanol is added to the remaining aqueous mixture, precipitating the acid quantitatively. This acid is removed by filtration with suction and recrystallized from glacial acetic acid (the recrystallized product then contains molecule of glacial acetic acid) or a water/glacial acetic acid mixture.

Yield: 60.5 pw=78% of theory, m.p. 233 to 234° C.
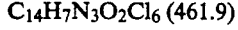$C_{14}H_7N_3O_2Cl_6$ (461.9)
Calc.: C 36.40%, H 1.53%, N 9.10%, Cl 46.05%.
Found: C 36.2%, H 1.35%, N 8.9%, Cl 46.5%.

EXAMPLE 19

Preparation of
3-(4,6-bis(trichloromethyl)-s-triazin-2-yl)cinnamic acid
(method b)

Analogously to Example 18, 67 pw 86% of theory of 3-(4,6-bis(trichloromethyl)-s-triazin-2-yl)cinnamic acid of melting point 210 to 211° C. (from glacial acetic acid/water) are obtained from 80 pw of methyl 3-(4,6-bis(trichloromethyl)-s-triazin-2-yl)cinnamate.

$C_{14}H_7N_3O_2Cl_6$ (461.9)
Calc.: C 36.40%, H 1.53%, N 9.10%, Cl 46.05%.
Found: C 36.1%, H 1.4%, N 8.9%, Cl 45.7%.

EXAMPLE 20

Preparation of propyl
4-(4,6-bis(trichloromethyl)-s-triazin-2-yl)benzoate
(method e)

4-(4,6-Bis(trichloromethyl)-s-triazin-2-yl)-benzoic acid (30 pw), n-propanol (14 pw), chloroform (220 pw) and toluenesulfonic acid (1.8 pw) are heated to reflux in a water separator. After about 12 hours, no more water separates. The mixture is allowed to cool, diluted with 400 pw of ether and washed twice with 5% strength sodium bicarbonate solution and twice with water. After drying over magnesium sulfate, the solvents are removed by distillation, and the residue is recrystallized from ethanol.

Yield: 25 pw of propyl 4-(4,6-bis(trichloromethyl)-s-triazin-2-yl)benzoate, m.p. 106 to 108° C.

$C_{15}H_{11}N_3O_2Cl_6$ (477.9)
Calc.: C 37.69%, H 2.32%, N 8.79%, Cl 44.50%.
Found: C 37.2%, H 2.1%, N 8.8%, Cl 44.6%.

EXAMPLES 21 to 25

According to Example 20, the following ester derivatives are prepared (method e):

EXAMPLE 21

2-Methoxyethyl 4-(4,6-bis(trichloromethyl)-s-triazin-2-yl)benzoate, m.p. 69 to 71° C.

EXAMPLE 22

Prop-(2)-ynyl 4-(4,6-bis(trichloromethyl)-s-triazin-2-yl)benzoate, m.p. 108 to 110° C.

EXAMPLE 23

Ethyl 3-(4,6-bis(trichloromethyl)-s-triazin-2-yl)benzoate, m.p. 113 to 115° C.

EXAMPLE 24

Propyl 4-(4,6-bis(trichloromethyl)-s-triazin-2-yl)cinnamate, m.p. 127 to 130° C.

EXAMPLE 25

Ethyl 3-(4,6-bis(trichloromethyl-s-triazin-2-yl)cinnamate, m.p. 100° C.

EXAMPLE 26

Preparation of
4-(4,6-bis(trichloromethyl)-s-triazin-2-yl)benzoyl
chloride (method c)

4-(4,6-Bis(trichloromethyl)-s-triazin-2-yl)-benzoic acid (87 pw) is added to thionyl chloride (350 pw). Upon heating to reflux in the absence of moisture and with vigorous stirring, a distinct evolution of $SO_2$ can be observed. After 6 hours, a clear solution is present. Excess thionyl chloride is distilled, towards the end by applying a vacuum. The residue containing in virtually quantitative yield pure 4-(4,6-bis(trichloromethyl)-s-triazin-2-yl)benzoyl chloride is recrystallized from hexane, m.p. 100 to 101° C.

$C_{12}H_4N_3OCl_7$ (454.3)
Calc.: C 31.72%, H 0.89%, N 9.25%, Cl 54.62%.
Found: C 31.9%, H 0.7%, N 9.3%, Cl 54.7%.

EXAMPLES 27 to 30

According to Example 26 the following acid chlorides and bromides are prepared (method c):

EXAMPLE 27

3-(4,6-Bis(trichloromethyl)-s-triazin-2-yl)benzoyl chloride, m.p. 102 to 103° C.

EXAMPLE 28

4-(4,6-Bis(trichloromethyl)-s-triazin-2-yl)cinnamoyl chloride, m.p. 156 to 158° C.

EXAMPLE 29

3-(4,6-Bis(trichloromethyl)-s-triazin-2-yl)cinnamoyl chloride, m.p. 177 to 178.5° C.

EXAMPLE 30

4-(4,6-Bis(trichloromethyl)-s-triazin-2-yl)benzoyl bromide. No exact determination of the melting point possible, since the product is extremely reactive and rapidly hydrolyzes in air. Reaction with absolute methanol gives the methyl ester, m.p. 157 to 158° C.

EXAMPLE 31

Preparation of
4-(4,6-bis(trichloromethyl)-s-triazin-2-yl)benzoic acid
(method d)

4-(4,6-Bis(trichloromethyl)-s-triazin-2-yl)-benzoyl chloride pw) is added to a mixture of tetrahydrofuran (10 pw) and water (5 pw). To complete the reaction, 1 pw of triethylamine is added after 6 minutes, and the mixture is stirred for another 10 minutes. The solvent is removed by distillation, and the residue is recrystallized from toluene/benzine. The product is identical with the compounds described in Examples 12 and 16.

EXAMPLE 32

Preparation of butyl
4-(4,6-bis(trichloromethyl)-s-triazin-2-yl)benzoate
(method f)

4-(4,6-Bis(trichloromethyl)-s-triazin-2-yl)-benzoyl chloride (9 pw) and n-butanol (1 pw) are added to dry toluene (100 pw). The mixture is stirred at 15° C., and 1.9 pw of pyridine is added dropwise. Stirring is continued for 3 hours. The resulting mixture is washed with 2% strength hydrochloric acid, 2% strength sodium hydroxide solution and then with water. After drying of the organic phase over magnesium sulfate, the solvent is removed by distillation, and the residue is recrystallized from ethanol. M.p. 109 to 110° C.

$C_{16}H_{13}N_3O_2Cl_6$ (492.0)
Calc.: C 39.06%, H 2.66%, N 8.54%, Cl 43.23%.
Found: C 38.6%, H 2.5%, N 8.6%, Cl 43.3%.

EXAMPLES 33 to 37

Analogously to Example 32, the following ester derivatives are prepared (method f):

EXAMPLE 33

Methyl 3-(4,6-bis(trichloromethyl)-s-triazin-2-yl)benzoate, m.p. 115° C. Compound identical with the product described in Example 2.

EXAMPLE 34

2-Phenoxyethyl 4-(4,6-bis(trichloromethyl)-s-triazin-2-yl)benzoate, m.p. 116 to 118° C.

EXAMPLE 35

4-Nitrophenyl-4-(4,6-bis(trichloromethyl)-s-triazin-2-yl)benzoate, m.p. 192 to 194° C.

EXAMPLE 36

Phenyl 4-(4,6-bis(trichloromethyl)-s-triazin-2-yl)cinnamate, m.p. 137 to 141° C.

EXAMPLE 37

Ethyl 3-(4,6-bis(trichloromethyl)-s-triazin-2-yl)cinnamate, m.p. 98 to 100° C.

WORKING EXAMPLE 38

A sheet made of electrolytically roughened and anodized aluminum is spin-coated with a coating solution comprising

| | |
|---|---|
| 6.7 | pw of trimethylolethane triacrylate |
| 6.5 | pw of a copolymer of methyl methacrylate and methacrylic acid, acid number 115, |
| 0.15 | pw of the compound of Example No. 37, |
| 64.0 | pw of 2-methoxyethanol, |
| 22.7 | pw of butyl acetate and |
| 0.3 | pw of 2,4-dinitro-6-chloro-2'-acetylamino-5'-methoxy-4'-(N-β-hydroxyethyl-N-β-cyanoethylamino)azobenzene | such that, after drying, a coating weight of 3.5 g/m² is obtained. The sheet is subsequently covered with a layer of polyvinyl alcohol and exposed under a line and halftone original to a 5 kW metal halide lamp for seconds. The exposed layer is developed by means of a 1.5% strength solution of sodium metasilicate.

The developed image is a negative of the original. Even very fine half tone and line elements have been clearly reproduced. Upon clamping the sheet into a sheet-fed offset press, 185,000 prints of high quality are obtained.

WORKING EXAMPLE 39

4-(4,6-Bis(trichloromethyl)-s-triazin-2-yl)cinnamoyl chloride (48 pw) are added to 5-(3,4-dimethoxyphenyl)-tetrazole-(2H) (20.6 pw) in pyridine (200 pw), and the mixture is slowly heated to reflux The solution turns dark with the evolution of nitrogen. After 2 hours, the solution is poured into ice water. The mixture of products is made weakly acidic with aqueous hydrochloric acid and extracted with a 1:1 mixture of diethyl ether and tetrahydrofuran, and the organic phase is dried over magnesium sulfate. After evaporation of the solvent, the mixture is taken up in toluene, after which a yellow residue insoluble in the solvent remains. This residue is isolated by filtration and is determined to be 2-[4-(4,6-bis(trichloromethyl)-s-triazin-2-yl)phenylethenyl]-5-(3,4-dimethoxyphenyl)-1,3,4-oxadiazole of melting point 241.5 to 242° C.

A coating solution according to Working Example 38 is prepared by substituting 0.25 pw of this compound for the compound of Example No. 37. Exposure and development gives an offset sheet with clean prints that, even after 200,000 prints, produces high quality.

WORKING EXAMPLE 40

3-(4,6-Bis(trichloromethyl)-s-triazin-2-yl)benzoyl chloride (22.7 pw) and N-ethyl-2-methyl-benzothiazolium-p-toluenesulfonate (15.5 pw) are suspended in toluene (150 pw). Triethylamine (13.1 pw) is added dropwise at 15° C. to this mixture. Stirring of the mixture is continued for 4 hours, the product is removed by filtration with suction, washed with methanol and then with water and then recrystallized from acetonitrile. This gives yellow crystals of 2-[3-(4,6-bis(trichloromethyl)-s-triazin-2 2-yl)benzoylmethylene]-N-ethylbenzothiazoline.

A coating solution according to Example 38 is prepared by substituting 0.25 pw of this compound for the compound of Example 37.

The processing described in Working Example 38 gives a negative image of the original that, even after a large number of prints, does not show any abrasion phenomena.

WORKING EXAMPLE 41

A coating solution according to Working Example 38 is modified such that, instead of compound No. 37, the following mixture in the amounts mentioned is used:
0.25 pw of compound No. 1
0.22 pw of dibenzalacetone (sensitizer)

The light-sensitive solution prepared is applied to an electrochemically-pretreated metal sheet and the sheet is dried to a dry coating weight of 2.2 g/m² The coating is then covered with a protective layer of polyvinyl alcohol. The sheet thus obtained is exposed for 30 seconds to a metal halide lamp through an original having fine line elements and a continuous-tone step wedge and is subsequently developed with the developer mentioned in Example 38. For comparison, a sheet is exposed under an edge filter which filters out the light components below 400 nm (edge filter 1) through the above-mentioned original, while increasing the time of exposure by a factor of 2. It is then developed.

The following fully-developed (hardened-through) steps are observed:

| Total Exposure | Edge Filter 1 |
|---|---|
| 4-5 | 4-5 |

The initiator according to the invention can thus be sensitized by suitable sensitizers for light of lower energy.

WORKING EXAMPLE 42

The procedure of Working Example 41 is repeated, except that the initiator mixture mentioned there is replaced by

| | |
|---|---|
| 0.25 | pw of compound No. 1 |
| 0.3 | pw of eosin |
| 0.6 | pw of a reaction product from 1 part of triethanolamine and 3 parts of butyl isocyanate. |

In addition to the above-mentioned exposures, the exposure takes place through an edge filter which filters out the light components below 450 nm (edge filter 2). The time of exposure is increased by a factor of 5 compared with standard exposure. After development, the following results are obtained:

| Total Exposure | Edge Filter 1 | Edge Filter 2 |
| --- | --- | --- |
| 5 | 4–5 | 4–5 |

This also shows that the initiator according to the invention can be activated for visible light by suitable sensitization.

What is claimed is:

1. A compound of formula I

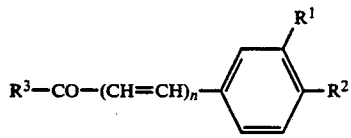

wherein $R^1$ and $R^2$ are different from one another and are either a hydrogen atom or a radical of the formula

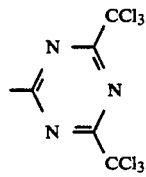

$R^3$ is an alkoxy radical having 1 to 16 carbon atoms which is unsubstituted or substituted by halogen atoms or phenyl groups, an alkynyloxy radical having b 2 to 4 carbon atoms, an alkoxyalkoxy radical having 3 to 10 carbon atoms which is unsubstituted or substituted by nitrogroups, an aryloxy radical having 6 to 14 carbon atoms which is unsubstituted or substituted by nitro groups, phenyloxyalkoxy radical having 8 to 12 carbon atoms, a hydroxyl group or a halogen atom, and denotes the number 0 or 1.

2. A compound as claimed in claim 1, wherein $R^3$ is an alkoxy radical having 1 to 6 carbon atoms, an alkenyloxy radical or alkynyloxy radical having 2 to 4 carbon atoms, a hydroxyl group or a chlorine atom.

3. A compound as claimed in claim 1, wherein $R^3$ is halogen.

4. A compound as claimed in claim 1, wherein $R^3$ is chlorine.

5. A compound as claimed in claim 1, wherein n is 0.

6. A compound as claimed in claim 1, wherein n is 1.

7. A compound as claimed in claim 1, wherein $R^3$ is a hydroxyl group.

8. A compound as claimed in claim 1, wherein $R^3$ is an alkoxy radical having 1 to 6 carbon atoms.

9. A compound as claimed in claim 1, wherein $R^3$ is an alkenyloxy radical having 2 to 4 carbon atoms.

10. A compound as claimed in claim 1, wherein $R^3$ is an alkynyloxy radical having 2 to 4 carbon atoms.

11. A compound as claimed in claim 2, wherein n is 0.
12. A compound as claimed in claim 3, wherein n is 0.
13. A compound as claimed in claim 4, wherein n is 0.
14. A compound as claimed in claim 7, wherein n is 0.
15. A compound as claimed in claim 8, wherein n is 0.
16. A compound as claimed in claim 9, wherein n is 0.
17. A compound as claimed in claim 10, wherein n is 0.

* * * * *